(12) United States Patent
Johns

(10) Patent No.: US 7,854,509 B2
(45) Date of Patent: Dec. 21, 2010

(54) VISION SCREENER

(76) Inventor: David Johns, 7 McDowell Way, Greenville, PA (US) 16125

( * ) Notice: Subject to any disclaimer, the term of this patent is extended or adjusted under 35 U.S.C. 154(b) by 172 days.

(21) Appl. No.: 12/206,159

(22) Filed: Sep. 8, 2008

(65) Prior Publication Data

US 2009/0153799 A1  Jun. 18, 2009

Related U.S. Application Data

(60) Provisional application No. 61/013,509, filed on Dec. 13, 2007.

(51) Int. Cl.
*A61B 3/14* (2006.01)
(52) U.S. Cl. .................................................. 351/206
(58) Field of Classification Search ................ 351/206, 351/208, 210, 212, 240, 205, 209, 211, 243, 351/246
See application file for complete search history.

(56) References Cited

U.S. PATENT DOCUMENTS

| | | | |
|---|---|---|---|
| 5,071,245 A * | 12/1991 | Fukuma et al. ............. 351/211 |
| 5,329,322 A | 7/1994 | Yancey |
| 6,089,715 A | 7/2000 | Hoover et al. |
| 6,523,954 B1 | 2/2003 | Kennedy et al. |
| 6,652,101 B1 | 11/2003 | Glaser |
| 7,290,882 B2 * | 11/2007 | Collins et al. .............. 351/218 |
| 7,391,887 B2 * | 6/2008 | Durnell ..................... 382/117 |
| 7,452,077 B2 * | 11/2008 | Meyer et al. ............... 351/205 |
| 7,670,002 B2 * | 3/2010 | Stark et al. ................. 351/205 |
| 7,686,451 B2 * | 3/2010 | Cleveland .................. 351/210 |

OTHER PUBLICATIONS

Simulation of Eccentric Photorefraction Images, Ying-Ling Chen, Bo Tan, and J.W.L. Lewis, Optics Express, vol. II, No. 14, Jul. 14, 2003.

* cited by examiner

*Primary Examiner*—Ricky L Mack
*Assistant Examiner*—Tuyen Q Tra
(74) *Attorney, Agent, or Firm*—James R. Williams

(57) ABSTRACT

An article and method for screening vision are described that does not require verbal input from a test person or the test person to maintain a fixed position during the screening. The article includes an image capture device, at least one test light, a processing unit that includes an interpretive program, and a display. The method comprises capturing an image of a person's eyes, verifying the image, studying the image, evaluating the image, and displaying the results. Conveniently, the article and method require no special training by an operator.

21 Claims, 3 Drawing Sheets

VISION SCREENER

The present invention claims priority to provisional application No. 61/013,509, which is hereby incorporated by reference.

FIELD OF THE INVENTION

The invention relates to a vision screening article and method and, more particularly to a vision screening article and method for persons who may be non-verbal or unable to understand or cooperate with a vision screening examination.

BACKGROUND OF THE INVENTION

Human vision includes an interaction of the eyes, which receive visual stimuli, and the brain, which creates clear images from the visual stimuli. This interaction is developed during early childhood and is usually complete by 6 to 8 years of age. Amblyopia is the term used to describe the condition when the vision in one eye is reduced because the interaction between the eye and the brain has not developed properly. This condition affects approximately 2-4% of the population. Untreated amblyopia can result in blindness in the affected eye. In fact, amblyopia is the leading reversible cause of blindness in children in the United States. Successful treatment of amblyopia includes early diagnosis.

Several underlying eye defects can lead to amblyopia. Amblyopia can be caused by strabismus, a misalignment in the positioning of the two eyes. Strabismus can cause the eyes to cross in (esotropia) or turn out (exotropia). Amblyopia can be caused by a significant difference between the refractive errors of the two eyes. Refractive errors include nearsightedness (myopia), farsightedness (hyperopia), or astigmatism. Occasionally, amblyopia is caused by other eye conditions such as opacities (cataract).

The American Academy of Pediatrics and other medical professional organizations recommend that children be screened for vision problems at least by age four. In many instances, correction of vision problems is possible through early diagnosis and treatment, but the diagnosis of non-verbal persons, such as infants, pre-school children, stroke victims, or mentally handicapped persons, can be difficult. Non-verbal persons may not realize or be able to communicate a visual problem. For this reason, many children may not have their vision screened before entering school at age five or six.

Several methods and systems exist for examining the vision of non-verbal persons. For example, a common method of screening vision in pre-school children is the use of an eye chart that is positioned at least ten feet from a child to be examined. Alternatively, the chart may be projected onto a surface or screen. An examiner points to optotypes (letters or symbols) that are displayed on the chart while one eye of the child is covered. A vision chart has several disadvantages in screening pre-school children for vision disorders. First, wall charts are not easily portable and require a special room or hallway to use. Secondly, a second examiner is usually required when using a vision chart if the child is too young to read letters or describe the appearance of the optotype symbols, or if the child otherwise cannot verbalize the correct response due to shyness or lack of understanding of the test. As one examiner stands at the chart and points to certain optotypes on the chart, the second examiner holds a second typically smaller chart at a closer proximity to the child. The second chart contains the same optotypes, but in a different arrangement. With one eye covered at a time, the child points to the optotypes on the second chart that correspond with the optotypes that the first examiner points to on the first chart. The second examiner is needed to monitor the child's responses. This method can give an approximate indication of the refractive error in the child's eyes but cannot indicate strabismus or opacities. This method is not effective for very young children.

Alternatively, an autorefractor can be used for detecting refractive errors in non-verbal persons. The autorefractor measures how light is changed by the person's eyes. Autorefractors can be large, costly, fixed units that constrain the person's head in a fixed position or hand-held, less costly, portable units that must be aimed and directed at the person by a trained operator. Fixed autorefractors require a person to assume and hold a fixed position and focus his eyes on the autorefractor. This can be difficult with children and other non-verbal persons. Portable autorefractors require a trained operator who will maintain a precise distance between the autorefractor and the person's eyes. Further, each eye must be tested separately. Autorefractors can be used to perform objective refraction of a child's eyes. The non-verbal person must look at a light emitting from the device, while the operator adjusts the device to focus the lens at the person's eyes, one at a time, thereby determining the prescription of each eye. An autorefractor measures only the refractive error of a person's eyes, and cannot indicate whether the person has a vision disorder such as strabismus or opacities.

Alternatively, a photoscreener can be used for vision screening. A photoscreener can be a fixed or portable device that produces a hard copy photograph or digitized image of a person's eyes as illuminated by a slightly off-axis flash. The photoscreener camera must be directed at a precise distance and direction with respect to the person's eyes and the person must look at the camera. An expert must evaluate the photographs and identify eye defects, such as gross refractive error, strabismus and opacities. Typically, results of a photoscreener exam are delayed until the photograph is developed and evaluated by an expert.

Electronic devices can also be used for vision screening. These typically capture and analyze an image of a single eye. The image-capturing camera must be placed at a roughly known distance from the person. The camera must be centered on a horizontally central landmark of the person, preferably the person's nose. The person is expected to face directly into the camera. Possible presence of opacities or strabismus can be determined by any method known to one skilled in the art. Possible presence of some degree of refractive error is determined by a photorefractive analysis of the models of the eyes found in the image. Inability to find the person's eyes or to analyze an image for any reason requires that the person be reexamined. Confirmation of possible indications of eye disorders also requires that the person be reexamined. False or missed indications of eye disorders are more likely if initial findings are not confirmed with analysis of additional images. Astigmatism cannot be detected from a single image captured in this manner.

Present vision screening technology typically requires the person to hold a fixed position and focus or to verbally interact with the screener. There is a need for a method and article for screening vision defects in non-verbal persons, including vision defects that manifest in early childhood. The method and article should be inexpensive, uncomplicated, and easily performed without special training. The method and article should not require verbal communication with the person, and should not constrain the person. Furthermore, the method and article should be quick, noninvasive, and painless.

SUMMARY OF THE INVENTION

The present invention describes a method and article for screening the vision of persons, particularly non-verbal persons or persons with limited attention spans such as, for example, young children. The invention requires no verbal interaction and little cooperation from the non-verbal person. The article can be integrated into an enclosure, does not require an operator to have extensive training, and does not constrain the position of the person. The method collects data from a plurality of images of the person's eyes, processes the data, and displays the results. Results can include vision defects such as, for example, a refractive error, a strabismus index, and opacity index.

DETAILED DESCRIPTION OF THE INVENTION

Figure 1:
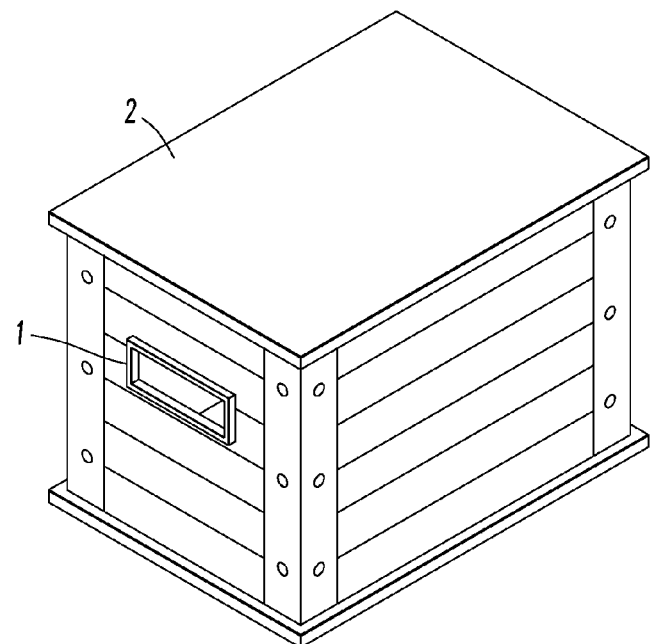
FIG. 1 shows a perspective view of an embodiment of the invention.

The invention describes a vision screening method and article. The invention permits the screening of a person's eyes without forcing the person into a constrained position, without significant verbal interaction with the person, and without the need for a skilled operator. The invention can be used to screen the vision of, for example, small children or other persons who may be non-verbal or who may be unable to understand or to cooperate with a vision screening examination.

The article includes an image capture device 6, a test light 7, a processing unit 34, and a display 3. The image capture device 6 focuses on a focal region 31. The focal region 31 is commonly near an aperture 1 defined by an enclosure 2. Practically, the aperture 1 is within 3 inches (7.62 centimeters) of the focal region 31 and preferably is within about 1 inch (about 2.54 centimeters) of the focal region 31. The article can include an enclosure 2 such as, for example, a box that defines an interior space 35. Optionally, the article can include an attention getting device 36 to encourage the person to look towards the image capture device 6. The attention getting device 36 can include, for example, flashing lights, pictures, sounds, noises, and combinations thereof. Conveniently, the interior space 35 of the enclosure 2 can accommodate the image capture device 6, the test light 7, the processing unit 34, and the attention getting device 36 while the enclosure 2 defines an aperture 1 substantially at the focal region 31.

Figure 3A:
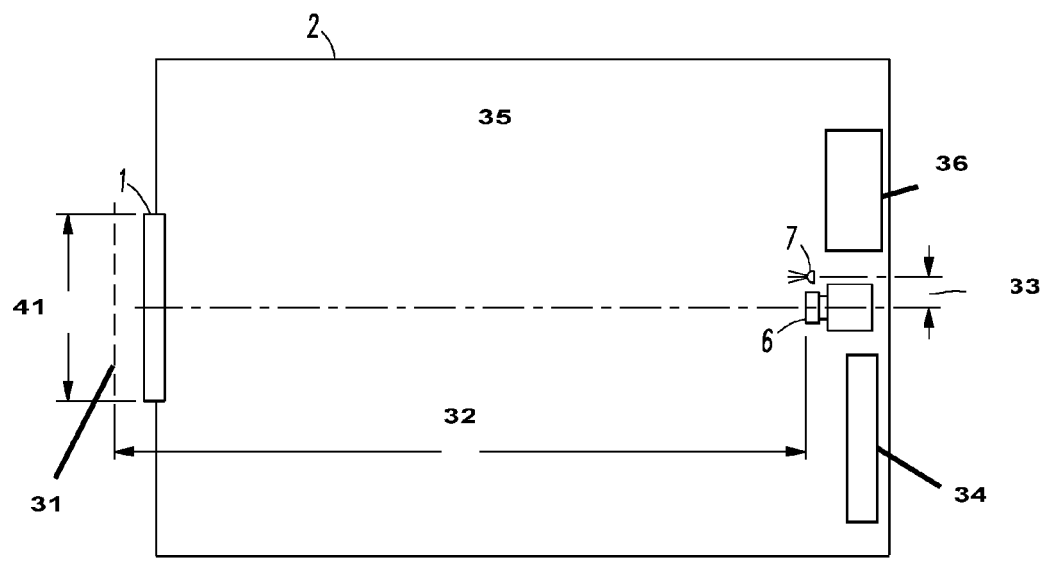
FIG. 3a is an interior top view of the enclosure of FIG. 1.
Figure 3B:
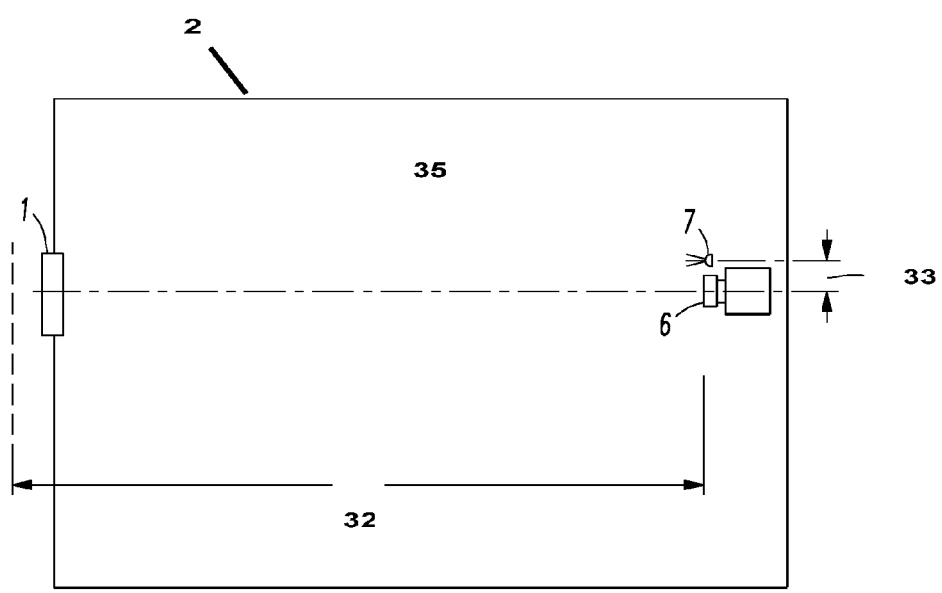
FIG. 3b is an interior side view of the enclosure of FIG. 1.

The image capture device 6 is focused on the focal region 31 at a focal distance 32 from the image capture device 6. At the focal distance 32, the image capture device 6 has a field of view 41 sufficient to include both of the person's eyes. The image capture device 6 can include, for example, a CCD digital camera, or other device for capturing digitized images. When the person's eyes are present at the focal region 31, the test light 7 illuminates the person's eyes for a sufficient time for the image capture device 6 to produce an image of the person's eyes. The capture time should have a shorter duration than the pupillary response time, that is, the person's pupils should not constrict substantially during image capture. As a result, capture times will typically be less than about ⅙ second. Shorter exposure times reduce the constriction of the person's pupils but require brighter test lights. A practical lower capture time is around ⅟₅₀₀ second. The test light 7 can include any device capable of producing a sufficiently bright light and can include, for example, an incandescent bulb, a flash bulb, a strobe, an LED, or combinations thereof. The test light 7 can be positioned near the camera. In the embodiment of FIGS. 3a and 3b, the test light 7 is mounted at an off-axis distance 33 from the image capture device 6, thereby producing an off-axis test light. The off-axis distance 33 will be sufficient to produce photorefraction. A convenient off-axis distance is at least about 0.25 inch (about 0.635 centimeter).

The focal region 31 occurs at a focal distance 32 from the image capture device 6. The focal distance 32 will depend on the image capture device 6. Conveniently, the focal distance will be at least about 12 inches (about 30.48 centimeters), preferably from about 12 inches (about 30.48 centimeters) to about 24 inches (about 60.96 centimeters), and more preferably from about 15 inches (about 38.1 centimeters) to about 17 inches (about 43.18 centimeters). The field of view 41 should be wide enough to capture both eyes of the person at the same time. To this end, the field of view 41 should be at least about 3.5 inches (about 8.89 centimeters) and preferably at least about 4.5 inches (about 11.43 centimeters). In one embodiment, an enclosure 2 is approximately 13 inches (approximately 33.02 centimeters)×13 inches (33.02 centimeters)×18 inches (45.72 centimeters), the aperture 1 is about 1.4 inches (about 3.556 centimeters) high and 4.5 inches (11.43 centimeters) long, the focal distance 32 is about 16 inches (about 40.64 centimeters), the field of view 41 is at least 4.5 inches (11.43 centimeters), and the off-axis distance 33 is about 0.5 inch (about 1.27 centimeters).

The article includes a display 3 and may include an input device 11. The input device 11 can include, for example, a keyboard, a touch-screen, or a magnetic device such as a flash drive, tape, or hard drive. The display 3 can include any tangible means of expression including, for example, electronic media, a monitor, printed media, a hard disc drive, a printer, a floppy drive, a flash drive, or combinations thereof.

The processing unit 34 is connected to at least the image capture device 6, the test light 7, the display 3, and when present the attention getting device 36 and the input device 11. The connections are typically wired but wireless connections are anticipated. The processing unit 34 controls the other elements of the article, and includes software that directs the capture of an image of a person's eyes, analyzes an image from the image capture device 6, and displays the analysis on the display 3. The processing unit 34 can comprise a general purpose computer or a dedicated processor, and so the software can be installed in RAM or ROM. The software includes the necessary commands and a database. The commands permit an operator to interface with the processing unit 34. The commands also perform the necessary steps for capturing, verifying, studying, and evaluating images. The database includes information relating to normal and abnormal eye conditions.

The processing unit controls and coordinates the actions of any test light, image capture device, attention getting device, input device, and display. Additionally, the processing unit can accept operator commands that are entered into the input device. Such commands can abort or change parameters of the vision screening, process images from the image capture device, and display the results of the vision screening examination.

The software can include a fuzzy logic expert system. The expert system includes a knowledge base of information from images of eyes with known refractive errors located in known image positions. In an embodiment, the knowledge base includes 17 items of information from 50 images with 10 specific refractive errors and with eyes in 15 specific image positions. In other words, the knowledge base includes 17 items of information from 7,500 (50×10×15) eye images and can determine specific vision defects such as, for example, refractive errors and indices strabismus and opacities, from image parameters. The number of items of information, refractive errors and image eye positions may be changed if further testing reveals better accuracy with other values.

In one example, the image capture device includes a ⅓ inch (7.62 centimeters) CCD, monochrome, medium resolution board camera with a 12 mm (0.4724 inch) lens. The test light includes two high-intensity LEDs. The attention getting device comprises a plurality of low-intensity LEDs and a sound generator. The processing unit comprises a general purpose computer. The input device comprises a keyboard, and the display includes a monitor and a printer. The computer is electrically connected via wires to the camera, test light, attention getting device, keyboard, monitor and printer. Software, which is loaded into the computer, controls operation of each element of the article. In operation, the person can move so that the person's eyes are at the focal region. The processing unit can detect the presence of the person's eyes, capture images of the person's eyes, analyze the images, and output the results.

The method for screening vision includes directing a person to look towards an image capture device 6 while the person's eyes are at the focal region 31. This will typically include directing the person to look into an aperture 1, capturing a plurality of images of the person's eyes, analyzing the images, and displaying the results of the vision screening. In embodiments, the method includes the steps of capturing, verifying, studying and evaluating images of a person's eyes when the person's eyes are illuminated by at least one test light. The results can be displayed to an operator.

Capturing includes obtaining a sufficient number of images of the person's eyes. More images produce increasing statistically significant results but increase the length of the test. A convenient number of images is from 3 to 10. The method can be statistically inconclusive with fewer than three captured images and more than ten images produce little increase in statistical significance. Capturing begins when the person looks towards the image capture device and the person's eyes are at the focal region. Conveniently, this can occur when the person looks into the aperture of an enclosure. Optionally, the article can display an attention getting device to direct the attention of the person. The attention getting device can include LEDs or similar light emitting devices, pictures, videos, sounds, etc. In one embodiment, the attention getting device includes a group of red LEDs positioned around the camera and visible when viewed through an aperture. The blinking lights are intended to draw the person's attention to the general location of the image capture device. Preferably, the blinking lights will be dim so that the pupils of the person's eyes do not constrict. The method can include a light meter that measures the light entering the aperture. Light levels below an established limit indicate that the person is in position at the aperture. The test can begin either automatically when the light level is below the established limit or manually on command from the operator. At time intervals, typically from about 1 to about 3 seconds, the article captures an image of the person's eyes. In one embodiment, capturing includes the following actions:

a. Detecting the person's eyes at a focal region;
b. Turning on a test light of sufficient luminosity to produce photorefraction in a captured image;
c. Capturing an image of the person's eyes with the image capture device;
d. Turning off the test light;
e. Transferring the captured image to a processing unit; and
f. Repeating steps (a) through (e) until a sufficient number of images are transferred or a predetermined maximum number of images are reached.

A sufficient number of images can be at least one, but a plurality of images is preferred. A convenient number is at least three, and a convenient maximum is about ten. More images produce more statistically reliable results. The number of images may be established by the operator. Image capture can be repeated as necessary to produce reasonably conclusive vision screening examination results. The minimum limit on the number of images captured is a matter of convenience. A minimum limit of about three is typical. A practical maximum limit of about ten is convenient to keep the examination time reasonable. Image capture can occur at relatively random interval or intervals so as to reduce the likelihood that the captured image will include a blink. To this end, the interval between image captures will typically be at least about one second.

The captured images can optionally be displayed to the operator so that the operator can observe the person looking at the image capture device. The images can be displayed in near real time or on time delay. The images that are displayed to the operator may be of any convenient size including, for example, actual size or thumbnail images. The test light can include at least one flash and may be directed towards the focal region. The test light can be positioned on approximately the same plane as the lens of the image capture device. The center of the test light can be at an off-axis distance from the center of the lens of the image capture device. The off-axis distance ensures the captured images illuminated by the test light show the person's eyes having photorefraction. The test light may be filtered to produce light in a narrow range of wavelengths in order to improve contrast in captured images. Capturing the image can include capture times sufficiently short so that pupil constriction is sufficiently small. Capture times will generally be less than ½ second, and preferably less than ⅙ second.

After the image is captured, the method verifies the captured image. Verifying includes ensuring that the captured image properly includes the person's eyes. Eyes are represented by flash reflections on or adjacent to the pupils. Images of eyes illuminated by a flash of light exhibit features that can be detected by image processing techniques known to one familiar with the art. Two features of each eye are important to the operation of the invention. These features are the corneal reflection, or bright spot that shows the flash reflection on the surface of the cornea, and the retinal reflex or circular area that shows the flash reflection through the pupil off the retina. These features should fall within a predetermined specification.

The corneal reflections in the images are found with peak point detection techniques. The retinal reflexes are found with edge detection techniques. A corneal reflection is comprised of one or more contiguous pixels that conform to an established pattern. Using analysis techniques such as, for example, fuzzy logic analysis, this pattern defines the expected range of height, width and brightness levels expected in a corneal reflection. A retinal reflex is comprised of the pixels enclosed by a circular edge that identifies the pupil of the eye. This edge circumscribes, or is adjacent to, a corneal reflection. The detection of this circular edge is complicated by the fact that pixels on either side of the detected edge may have a very wide range of light levels. Pixels in the iris of the eye that surrounds the pupil may range from very bright for light blue eyes to very dark for dark brown eyes. Pixels within the pupil may exhibit a wide range of light levels depending on the pattern of light reflected off the retina. In the preferred embodiment of the invention, the corneal reflection pattern and the retinal reflex edge parameters are established through the observation of a plurality of images of eyes that exhibit known corneal reflections and retinal reflexes.

The retinal reflex exhibits a wide range of light levels due to the optical phenomena known as photorefraction. The retinal reflex of normal eyes, that is eyes with no refractive error, exhibit a very uniform circular light pattern. The retinal reflex of eyes that have some degree of refractive error exhibit a crescent shape of brighter light levels at one side of the retinal reflex. This crescent shape is caused by photorefraction. The size, position and brightness of the crescent shape within the retinal reflex accurately indicate the degree and type of refractive error in the eye. At least one attribute, and preferably a plurality of attributes, is determined for both right eye and the left eye based on the corneal reflection and corresponding retinal reflex for each eye in the image. These attributes include:
  a. the X- and Y-coordinates of the corneal reflection;
  b. the X- and Y-coordinates of the retinal reflex; and
  c. the diameter of the retinal reflex.

In addition to the attributes, several conditions will exist before the attributes can be considered valid. These conditions include:
  a. attributes for exactly two (2) eyes are determined;
  b. the retinal reflex of the right eye must be located in the left portion of the image bounded by convenient top, bottom, left and right boundary limits;
  c. the retinal reflex of the left eye must be located in the right portion of the image bounded by convenient top, bottom, left and right boundary limits;
  d. the retinal reflexes of the right and left eyes must be separated by a distance within convenient minimum and maximum limits;
  e. the diameter of each retinal reflex must be within convenient minimum and maximum values; and
  f. the right and left retinal reflexes must have diameters that are within a convenient maximum difference in size.

If any of these conditions are not met, the attributes are not valid and the computer implemented process returns to the previous step where the image capture process is repeated. If all conditions are met, the attributes are valid. In this case, the count of valid images is incremented and the computer implemented process continues below to determine optical characteristics.

In one embodiment, verifying includes the following elements:
  a. Finding a flash reflection on the person's right eye in the left portion of the image. The location of this reflection will be in a left boundary limit as defined by established upper, lower, right and left position limits;
  b. Finding a flash reflection on the person's left eye in the right portion of the image. The location of this reflection will be in a right boundary limit as is defined by established upper, lower, right and left position limits as well as a limit on the minimum distance from the right eye flash reflection;
  c. Finding pupils on or adjacent to both the left and right eye flash reflections.

Each pupil must be circular in shape and have a diameter within established maximum and minimum limit values; and
  d. Ensuring the diameters of both pupils are substantially the same.

In this embodiment, the image is verified if conditions a, b, c, and d are met. If unverified, the image may be rejected as unsuitable for subsequent evaluation. When an image is verified, the process moves to the studying step. If a sufficient number of images are not yet verified, the number of images captured thus far during the test is checked. If less than a predetermined maximum limit of images has been captured, the article captures another image. The maximum limit is a matter of convenience. The number of images captured during the exam can be displayed to the operator. A maximum limit of about ten is typical. If the maximum limit of images has been captured without at least verifying the minimum number of verified images, the test is deemed inconclusive. The test may be repeated or the person may be referred to a health care professional.

Once a sufficient number of images are verified, the images are studied. Studying includes identifying at least one vision parameter and preferably a plurality of vision parameters. The vision parameters are used to determine optical characteristics relating to strabismus, opacities and refractive errors of eyes. Strabismus is the condition in which the eyes are misaligned and unable to point in the same direction at the same time. A convenient strabismus index is established in which normally aligned eyes have a strabismus index of zero (0), converged eyes have a positive strabismus index, and diverged eyes have a negative strabismus index. Opacities are occlusions of the clear refractive media of the eye that degrade the light passing through the eye to the retina. A convenient opacities index is established in which eyes with no occlusion have an opacities index of zero (0) and eyes with some degree of occlusion have a positive opacities index. Refractive error is the difference between the focal length of the cornea and lens of an eye and the length of the eye. The refractive error of an eye is expressed as the lens power, measured in diopters, needed to correct vision in the eye. A normal eye, that is one that needs no correction, has a refractive error of zero (0). The refractive error of a myopic eye is a negative number. The refractive error of a hyperopic eye is a positive number.

The strabismus index of a person's eyes measures the degree to which the relative center positions of the cornea and pupil of the dominant eye differ from the relative center positions of the cornea and pupil of the subordinate eye. There is essentially no difference in these relative center positions in eyes that have no significant evidence of strabismus. In this case, the strabismus index of the eyes is zero (0). Positive or negative values for this difference in relative center positions indicate some degree of divergence or convergence of the eyes. In these cases, the strabismus index is a numerical value that represents the extent and type of misalignment of the eyes. Since this technique measures the relative difference in the positions of the centers of the dominant and subordinate corneas and pupils, the strabismus index can be found regardless of where in the image the eyes are found and independent of whether or not the person's eyes are directed at the camera. In the preferred embodiment of the invention, positive strabismus index values from 1 to 5 indicate increasingly divergent eyes. Negative values from −1 to −5 indicate increasingly convergent eyes.

The opacities index of each of the person's eyes measures the degree to which discrete bright or dark areas exist in the circular pupil of the eye. Pupils of eyes with no evidence of opacities exhibit a uniform light intensity or a consistent gradient of light intensities with no discrete light or dark areas. In this case, the opacities index is zero (0). Light or dark areas in the normally uniform or consistent pupil are evidence of occlusions that degrade the light passing through the eye. In this case, the opacities index is a value that represents the amount of occlusion in the eye. The light or dark areas in the pupil are detected regardless of where in the image the eyes are found and independent of whether or not the person's eyes are directed at the camera. In the preferred embodiment of the invention, opacities index values from 1 to 5 indicate increasingly occluded eyes.

The refractive error of an eye is a measure of the difference between the focal length of the cornea and lens of the eye and the length of the eye. Refractive error is determined by the photorefraction characteristics exhibited in the pupil of the eye. A normal eye, that is one that has no refractive error, exhibits a very uniform range of light intensities in the pupil. An eye with a refractive error exhibits a distinct crescent shaped reflection in the pupil. The existence and characteristics of this crescent shaped reflection are determined by examining the light intensities along and near a diameter of the pupil that is on the same axis as the high intensity flash by which the eye was illuminated during image capture. The size, position, and intensity of the crescent shaped reflection accurately determine the type and degree of refractive error when the position of the eye in the image is known. But, because the eye may be at any position in the image, an expert system process determines refractive error given specific crescent shaped reflection characteristics and eye position in the image. This process determines refractive error regardless of where in the image the eye is found and independent of whether or not the person's eyes are directed at the camera.

Studying includes identifying vision parameters comprising:
 a. Identifying the X- and Y-coordinates of the center of the flash reflection and pupil for each eye;
 b. Defining a horizontal mid-line through the center of each eye's pupil based on the X- and Y-coordinates; and
 c. Determining the refractive error and opacity index for each eye and the strabismus index for both eyes when considered together.

The strabismus indicator, opacity indicator, and refractive error findings of the study can be displayed to the operator. If the number of images studied is less than the minimum number of studied images necessary for a conclusive examination, the image capture method can be repeated. If the number of images studied equals the minimum number of studied images necessary for a conclusive examination, the studied images can be evaluated.

Refractive error, opacity index, and strabismus can be determined by any method known to one skilled in the art. For example, refractive error can be determined using a photorefraction technique. Photorefraction is a well-established technique for relating the shape of a nearly on-axis light reflected off an eye's retina to the refractive error in the eye. When the position of the eye with respect to the image capture device and the test light that illuminates the eye are precisely known, the photorefraction technique can determine specific refractive error in the eye. However, with respect to the present invention, the aperture through which the images of the person's eyes are illuminated and captured does not constrain the person to such a precise position. The method for determining refractive errors, regardless of the positions of the eyes in the image, includes an expert system, programmed into the processing unit, which can determine the refractive errors regardless of the positions of the eyes.

The expert system determines refractive error, and preferably comprises an inference engine that uses fuzzy logic. Fuzzy logic includes a set of rules that compare the position and photorefraction characteristics of an eye against a knowledge base. The fuzzy logic inference engine is capable of using data that has been collected from imprecise measurements. Fuzzy logic means a mathematical logic that extends normal boolean True/False set membership values to allow values anywhere within the range 0 to 1. Specifically, fuzzy logic allows assignment of some value from 0 if False to 1 if True, or some value between 0 and 1 if "Somewhat True." A fuzzy logic inference engine and rules are able to generate results despite imprecise data, such as the position of the person.

The photorefraction technique includes:
 a. Identifying the position of the center of the pupil with respect to the center of the image;
 b. Indexing the position of the center of the pupil;
 c. Determining the average light level at each position near the horizontal mid-line through the center of the pupil;
 d. Determining the average light levels in at least sixteen substantially equally sized sections along the pupil mid-line;
 e. Using the sections' mid-line light levels and the position index to access a database of known refractive error located at known positions in the image; and
 f. Determining the most likely refractive error value based on the database.

The opacities index for each eye can be found by identifying and quantifying non-uniform brightness level variations in the pupil, such as by:
 a. Identifying areas near the mid-line through the center of the pupil where darker brightness levels are completely surrounded by lighter brightness levels;
 b. Counting the number of areas where a darker brightness level is surrounded by higher brightness levels; and
 c. Converting the dark area count to an opacities index value;

The strabismus index for the eyes can be found by measuring the alignment of the flash reflection positions with respect to the pupil positions. The following steps may be used to find the strabismus index for the eyes.
 a. Identifying the horizontal and vertical offsets from the center of the flash reflection to the center of the pupil for each eye;
 b. Determining the differences between the horizontal and vertical offsets; and
 c. Converting the offset differentials to a strabismus index value.

The results from the studied images can be displayed to the operator, stored in an electronic medium, or printed.

Evaluating the studied images includes producing a test result that may include a vision defect. The test result is determined by comparing the vision parameters from the studied images to known normal limits on eye defects. The test result can include information on one or more vision defects, and can include detailed or summary information. For example, an embodiment could produce only a summary of the test result identifying the test result as inconclusive, normal, or abnormal. Inconclusive indicates either that fewer than three captured images were successfully verified and studied or that the operator manually stopped the test. Normal indicates that the evaluation of the images did not indicate a high likelihood of vision problems. Abnormal indicates that one or more vision defects may exist, and indicates follow up with a health care professional may be necessary. Vision defects can include:
a. a refractive error beyond established limits in one or both eyes.
b. a refractive error differential between the two eyes that exceeds an established limit.
c. a high level of opacities in one or both eyes.
d. a possibility of strabismus, a high level of misalignment between the two eyes.

The operator may conclude, continue, or cancel the test after the evaluating step. The operator may save the test results, such as to electronic or print media, or discard the results.

EXAMPLE 1

Figure 2:
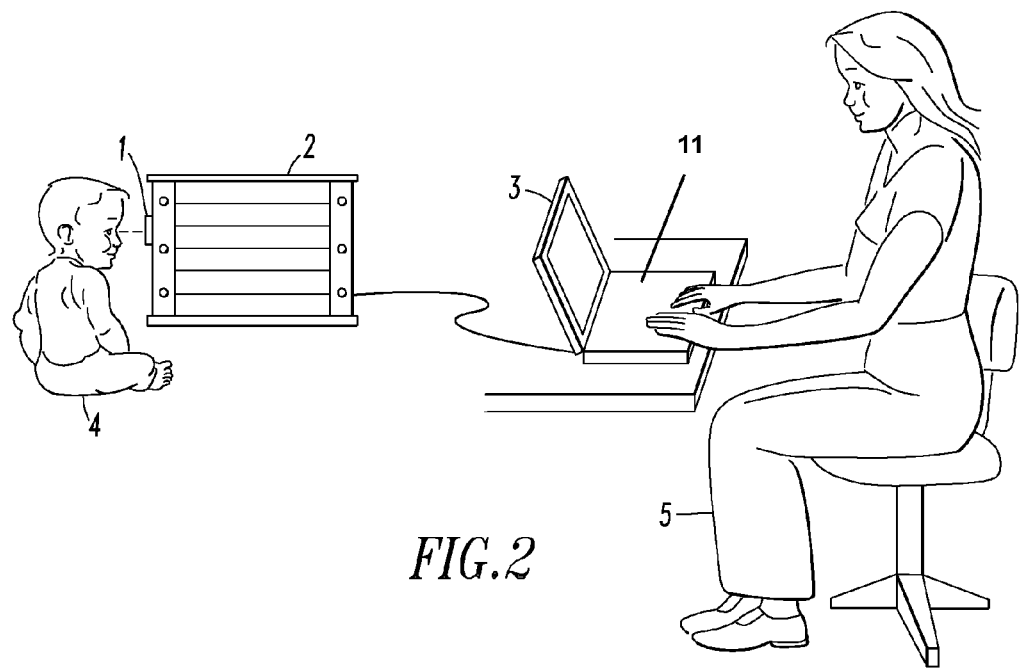
FIG. 2 shows a physical relationship of an embodiment of the invention as used by an operator to perform a vision screening examination on a person.

A person's eyes were tested using the method and article of the invention. The article included an enclosure defining an aperture. The enclosure was configured to appear as a treasure chest. The article comprised components including an attention getting device, an image capture device, a test light, a processing unit, an input device, a printer, and a display. Conveniently, the attention getting device, the image capture device, the test light, the processing unit, and the printer were contained within the enclosure. An operator entered the person's name using a keyboard input device. The operating program permitted as many as twenty-five characters as either text, numbers or special characters. The operator entered the person's birth date in the format mmddyy where mm is the month, dd is the day and yy is the year of the birth date. Pressing the [Esc] key permitted correction of any mis-entries. The display was an LCD monitor and the display projected the person's name, birth date, approximate age in years and months, and the date and time at the start of the exam. The operator activated the attention getting device, which consisted of a pattern of blinking lights that was visible through the aperture. The operator directed the person to look through the aperture at the blinking lights. The person, who was under two years of age, was assisted as necessary. The image capture device displayed a thumbnail of the aperture on the monitor. The operator started the exam by pressing the [Enter] key. Optionally, the article could have included a photocell that would have started the exam when the ambient light through the aperture had decreased below a predetermined level. The article captured a plurality of images of the person's eyes. A processing unit analyzed the images and defined several attributes of each eye's pupils. Using a photorefraction technique, the processing unit then determined the refractive error and opacity index for each eye and the strabismus index for both eyes when considered together. The data included 17 items of information from at least three eye images for the person. The processing unit included a fuzzy logic expert system. The fuzzy logic expert system included a database of 7,500 images of eyes with 10 different known refractive errors appearing in 15 known areas of the images. The computer program compared the results of the exam to normal values and identified the results as either inconclusive, normal or abnormal. The results were displayed to the operator as shown in FIG. 2. The operator saved the results in an electronic medium and printed a paper copy.

EXAMPLE 2

A person's eyes are examined using the following method. The method begins when the person's eyes look into an aperture. The aperture is large enough to allow the person to assume a wide range of viewing positions such that the person is not constrained to a fixed or forced position. The method includes:
a. capturing a plurality of images of the person's eyes when presented at the aperture;
b. verifying that captured images include both eyes of the person;
c. studying a plurality of verified images to calculate and present findings of strabismus indicators, opacity indicators, refractive errors, or other defects in the person's eyes; and
d. evaluating the studied images to determine and present the study findings as normal, abnormal, or inconclusive, and to present an indication if the person should be referred for a follow-up examination by an ophthalmologist or other vision professional.

EXAMPLE 3

A method for capturing images begins when a person looks into the aperture of an enclosure. The method includes the following steps:
a. activating an attention getting device;
b. testing the light level to ensure the presence of a person at the aperture;
c. allowing an interval of time, typically from about 1 to 3 seconds, to pass so that the timing of the remaining steps will be unpredictable to the person;
d. activating a test light, optionally filtered to produce light in a limited frequency range, for a time period shorter than the person's pupillary response time and at an intensity bright enough to produce photorefraction in an image of the person's eyes;
e. activating an image capture device, while the test light is activated, to capture the image present at the aperture;
f. transferring the captured image to a processing unit for verification; and
g. deactivating the attention getting device.

EXAMPLE 4

In one embodiment of the invention, an operator entered the person's name and birth date using a keyboard. The person's gaze was attracted to an attention getting device that was observable through an aperture in an enclosure. The aperture was located at a focal region of an image capture device. The article displayed a continuous live view of the aperture on a video screen. After random time intervals of approximately 1-3 seconds, a test light illuminated the person's eyes and an image capture device captured an image of the person's eyes. The number of images captured during the examination was incremented and displayed to the operator. A processing unit verified that the images were suitable for evaluation. Verification included ensuring that each image included a test light reflection on or near each circular pupil, the pupil diameters were essentially the same size and within established maximum and minimum size limits, and the distance between the pupils was within established maximum and minimum values. The test progressed until at least three verified images were obtained. The processing unit then evaluated verified images. Evaluation included finding the X- and Y-coordinates of the center of the test light reflection for each eye, determining the X- and Y-coordinates of the center of the pupil of each eye, converting the X- and Y-coordinates of the center of each pupil into an index value (1-15) of the eye's position in a region of 3 rows and 5 columns corresponding to the image of the aperture, finding the horizontal mid-line through the center of each pupil, finding values for the number and size of regions of low light level intensity completely surrounded by regions of higher light level intensity on or near the horizontal mid-line through the center of each pupil, and finding values for the light intensity levels in 16 equal sized regions on or near the horizontal mid-line through the center of each pupil. The strabismus indicator for the eyes was determined by quantifying the difference between the X- and Y-coordinate positions of the centers of the flash light reflections and the pupils for the eyes, and comparing this quantified difference to established minimum and maximum values. A quantified difference lower than the established minimum value indicated a convergence of the eyes known as esotropia, a form of strabismus. A quantified difference higher than the established maximum value indicated a divergence of the eyes known as exotropia, a form of strabismus. The opacity indicators for both eyes were determined by quantifying the number and size of regions of low light level intensity completely surrounded by regions of higher light level intensity on or near the horizontal mid-line through the center of each eye's pupil, and comparing these quantified values to established maximum values. Quantified values greater than established maximum values indicate opacities. Refractive errors for both eyes were determined by evaluating the 16 light intensity level values on or near the horizontal mid-line through the center of each eye's pupil. These values and the index value of the eye's position were used as input data to an expert system. The expert system used a fuzzy logic inference engine to compare the values against a knowledge base that includes fuzzy logic functions for eyes with 10 known refractive errors as found in 15 different positions in the image. The fuzzy logic expert system determined refractive error regardless of the position of the eye in the image. The strabismus indicator, opacity indicator, and refractive error study findings were displayed to the operator. The operator concluded the examination by printing a hard copy report that includes the person's name and birth date as well as the examination details, summary, and results.

EXAMPLE 5

Figure 4:
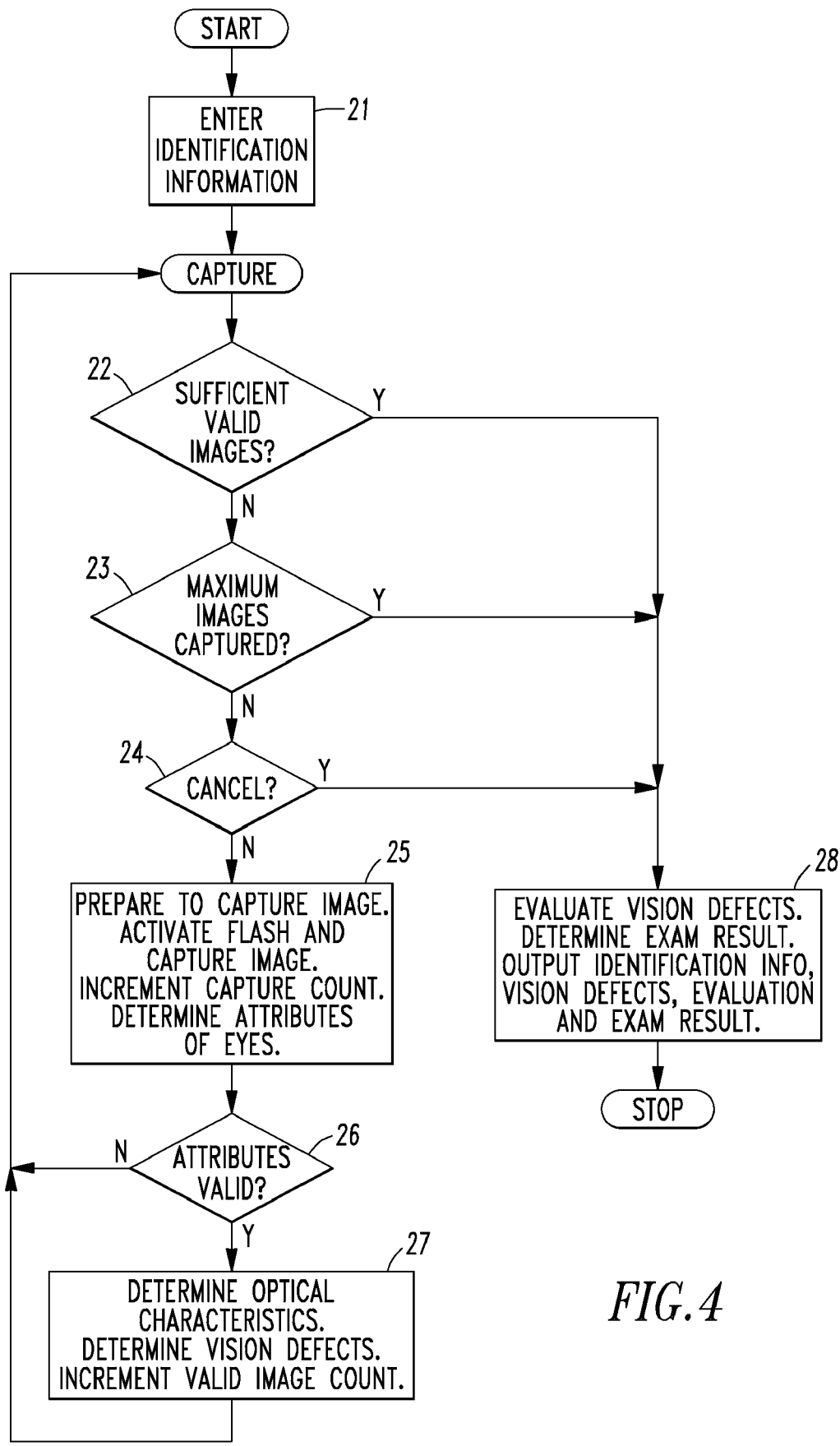
FIG. 4 is a flow chart of an embodiment of the vision screening examination method.

FIG. 4 shows a flow chart for a method of the invention. The operator starts the method by entering 21 identifying information into the input device. The method captures 25 an image of the person's eyes. The method validates 26 or rejects the image. If validated, the image is studied 27. If either a sufficient number of images have been captured 22 or the maximum number of images have been captured 23, the method analyzes 28 the images and displays the results. If any insufficient number of images is validated after a predetermined number of trials, the test is canceled 24 and the failure is displayed 28.

Numerous modifications and variations of the present invention are possible. It is, therefore, to be understood that within the scope of the following claims, the invention may be practiced otherwise than as specifically described. While this invention has been described with respect to certain preferred embodiments, different variations, modifications, and additions to the invention will become evident to persons of ordinary skill in the art. All such modifications, variations, and additions are intended to be encompassed within the scope of this patent, which is limited only by the claims appended hereto.

What is claimed:

1. A method of vision screening a person's eyes including a right eye and a left eye, the method comprising:
    a) Capturing at least one image of the person's eyes;
    b) Verifying the image includes the right eye and the left eye;
    c) Studying the image for vision parameters; and
    d) Evaluating the vision parameters to determine a vision screening result, and, wherein verifying includes ensuring:
        (i) A right eye retinal reflex is located in a left portion of the image within left boundary limits;
        (ii) A left eye retinal reflex is located in a right portion of the image within right boundary limits;
        (iii) The right eye retinal reflex and the left eye retinal reflex are separated by a distance within minimum and maximum limits;
        (iv) The diameters of the right eye retinal reflex and the left eye retinal reflex are within minimum and maximum values; and
        (v) The right eye retinal reflex and the left eye retinal reflex have diameters that are within a maximum difference in size.

2. The method of claim 1, wherein capturing includes capturing the image with an image capture device while illuminating the person's eyes with a test light that is at an off-axis distance from the image capture device.

3. The method of claim 2, wherein illuminating the person's eyes is of a shorter duration than a pupillary response time and of a brightness sufficient to produce photorefraction in the image of the person's eyes.

4. The method of claim 2, wherein the method includes attracting the person's eyes towards the image capture device before capturing the image.

5. The method of claim 1, wherein the method includes capturing a plurality of images.

6. The method of claim 5, wherein capturing includes a delay of a random interval between capturing the images.

7. The method of claim 1, wherein capturing includes
    a. Detecting the person's eyes at a focal region;
    b. Illuminating the person's eyes with a test light of sufficient luminosity to produce photorefraction;
    c. Capturing the image of the person's eyes with an image capture device; and
    d. Transferring the image to a processing unit.

8. The method of claim 7, wherein capturing includes repeating steps (a) through (d) until a sufficient number of images are transferred.

9. The method of claim 1, wherein verifying includes identifying at least one attribute each for the right eye and the left eye and ensuring the attribute is within a specification, the attribute being selected from a group consisting of a retinal reflex diameter, X- and Y-coordinates of a corneal reflection, X- and Y-coordinates of the retinal reflex, and combinations thereof.

10. The method of claim 1, wherein each eye includes a corneal reflection and a retinal reflex, and studying comprises determining vision parameters including:
    a. Identifying for each eye X- and Y-coordinates of centers of the corneal reflection and the retinal reflex; and
    b. Identifying for each eye a horizontal mid-line through a center of the retinal reflex based on the X- and Y-coordinates.

11. The method of claim 1, wherein evaluating includes comparing the vision parameters with a database to determine a vision defect, and displaying the vision defect as the vision screening result.

12. The method of claim 11, wherein the database includes a plurality of vision defects as functions of the vision parameters.

13. The method of claim 12, wherein the plurality of vision defects include a group consisting of a strabismus index, a refractive error, an opacity index, and combinations thereof.

14. The method of claim 1, wherein evaluating includes an inference engine that uses a database and a set of rules to match the vision parameters to a vision defect.

15. The method of claim 1, wherein the method includes displaying the vision screening result.

16. A method of vision screening a person's eyes including a right eye and a left eye, the method comprising:
   a. Detecting the person's eyes at a focal region;
   b. Illuminating the person's eyes with an off-axis test light of sufficient luminosity to produce photorefraction;
   c. Capturing an image of the person's eyes with an image capture device;
   d. Transferring the image to a processing unit;
   e. Verifying the image with the processing unit by identifying at least one attribute each for the right eye and the left eye and ensuring the attribute is within a specification, the attribute being selected from a group consisting of a retinal reflex diameter, X- and Y-coordinates of the retinal reflex, X- and Y-coordinates of a corneal reflection, and combinations thereof, wherein verifying also includes:
      ensuring that the image includes the right eye and the left eye;
      (i) A right eye retinal reflex is located in a left portion of the image within left boundary limits;
      (ii) A left eye retinal reflex is located in a right portion of the image within right boundary limits;
      (iii) The right eye retinal reflex and the left eye retinal reflex are separated by a distance within minimum and maximum limits;
      (iv) The diameters of the right eye retinal reflex and the left eye retinal reflex are within minimum and maximum values; and
      (v) The right eye retinal reflex and the left eye retinal reflex have diameters that are within a maximum difference in size;
   f. Studying the image for vision parameters by identifying for each eye (i) X- and Y-coordinates of centers of the corneal reflection and (ii) a horizontal mid-line through a center of a pupil of each eye based on the X- and Y-coordinates;
   g. Using an inference engine to evaluate the vision parameters against a database to determine a vision screening result; and
   h. Displaying the vision screening result.

17. An article for the screening a person's eyes including a right eye and a left eye comprising:
   a. An image capture device for capturing an image of the person's eyes at a focal region;
   b. A test light for illuminating the person's eyes at the focal region;
   c. A processing unit for verifying, studying, and evaluating the image; and
   d. A display for displaying a vision screening result, wherein verifying includes:
      (i) ensuring that the image includes the right eye and the left eye;
      (ii) A right eye retinal reflex is located in a left portion of the image within left boundary limits;
      (iii) A left eye retinal reflex is located in a right portion of the image within right boundary limits;
      (iv) The right eye retinal reflex and the left eye retinal reflex are separated by a distance within minimum and maximum limits;
      (v) The diameters of the right eye retinal reflex and the left eye retinal reflex are within minimum and maximum values; and
      (vi) The right eye retinal reflex and the left eye retinal reflex have diameters that are within a maximum difference in size.

18. The article of claim 17, wherein the article includes an enclosure defining an interior space and an aperture near the focal region, the image capture device within the interior space.

19. The article of claim 17, wherein the test light is at an off-axis distance from the image capture device.

20. The article of claim 17, wherein the article includes an input device.

21. The article of claim 17, wherein the article includes an attention getting device.

* * * * *